United States Patent [19]

Dragan

[11] Patent Number: 4,492,576
[45] Date of Patent: Jan. 8, 1985

[54] DENTAL SYRINGE AND METHOD OF PACKAGING AND DISPENSING A DENTAL MATERIAL

[76] Inventor: William B. Dragan, R.F.D. 1 Burr St., Fairfield, Conn. 06430

[21] Appl. No.: 388,649

[22] Filed: Jun. 15, 1982

[51] Int. Cl.³ .......................... A61C 5/04; A61M 5/31
[52] U.S. Cl. ........................................ 433/90; 604/61; 604/218; 604/311
[58] Field of Search ...................... 433/80, 81, 89, 90; 604/38, 61, 187, 218, 222, 223, 232, 233, 311; 222/323, 325, 326, 386

[56] References Cited

U.S. PATENT DOCUMENTS

| 2,294,954 | 9/1942 | Brady | 222/326 X |
| 2,505,028 | 4/1950 | Boeger | 433/90 |
| 3,766,918 | 10/1973 | Kessel | 604/222 X |
| 3,974,831 | 8/1976 | Malmin | 433/90 X |
| 4,338,925 | 7/1982 | Miller | 604/61 X |
| 4,391,590 | 7/1983 | Dougherty | 433/90 |

Primary Examiner—Robert P. Swiatek
Attorney, Agent, or Firm—Arthur T. Fattibene

[57] ABSTRACT

A dental syringe and a method of packaging and dispensing a dental material wherein the package containing the dental material comprises a cartridge containing a bulk supply of dental material, and which cartridge is constructed so as to function as a syringe for effecting the extrusion of the dental material therefrom as may be needed in a dental restorative procedure. The cartridge comprises an elongated tubular barrel having an open end portion and a forward discharging orifice portion through which the material is extruded. A displaceable piston seals the rear end of the barrel to confine the dental material within the barrel, and which cartridge can be readily attached to a handle and associated plunger to complete a syringe assembly. The plunger is also provided with a device for relieving the back pressure imparted to the cartridge piston during an extruding operation to prohibit any unwanted drooling of the material therefrom. The associated plunger may also be adjustably extended to effect total extrusion of the material from the cartridge in predetermined incremental amounts.

14 Claims, 9 Drawing Figures

DENTAL SYRINGE AND METHOD OF PACKAGING AND DISPENSING A DENTAL MATERIAL

BACKGROUND OF THE INVENTION

The present invention relates to improvements in dental syringes of the type disclosed in my prior U.S. Pat. Nos. 3,436,828; 3,581,399; 3,900,954; 4,198,756; Des. 226,767 and co-pending patent application Ser. No. 314,768, filed Oct. 26, 1981, which are particularly adapted for precisely positioning various composites and/or other viscous dental material in a dental restorative procedure. Heretofore, such dental materials have been packaged in jars and other containers which a dentist would purchase in bulk, and which then required the dentist to parcel out of the bulk supply in small amounts the material necessary for a particular procedure. As a result, a dentist had to rely on his judgement to ascertain how much material was needed for a particular procedure. This trial and error method of determining the amount of material necessary, more frequently than not, proved to be wasteful practice because invariably more material than was necessary would be mixed or used. As such materials may be relatively costly, any amount so wasted only increased a dentist's operating costs.

Also, the taking of such material from a bulk supply to the placement of the material to a patient's tooth is a tedious and time-consuming operation and oftentimes resulting in voids occurring in the filling of a tooth cavity, by the spatuling of such material into a cavity. The syringe constructions as disclosed in the foregoing noted patents were conceived to enhance the application of such current dental materials in a dental procedure and required the dentist to first parcel out the amount of material required and load the syringe with such amount.

The objects of the present invention are intended to further advance the art of restorative dentistry and the packaging and dispensing of various dental materials such as the viscous composite resins, impression materials, light activated materials and the like. The light activated materials, in particular, pose the additional problem that such material, when exposed to light will tend to set or cure in a relatively short period of time. Therefore, the dispensing of such light activated material from a bulk supply presented a further handling problem, viz. the exposure of such material to curing light in effecting the transfer of the material from its bulk supply to the patient's mouth.

OBJECTS

A particular object of this invention resides in an improved syringe construction in which the bulk supply of the dental material is packaged in a cartridge which functions as the dispensing barrel of a syringe whereby the dental material can be extruded directly from the bulk supply as may be needed thereby minimizing all waste and/or the trial and error method of determining the amount of material needed for a given procedure.

Another object of this invention is to provide a package for containing a bulk supply of light activated dental material or other viscous dental material whereby the material can be readily dispensed from the bulk supply to the patient's tooth as needed and without undue exposure to light and/or contaminating influences.

Another object is to provide an improved dental syringe in which any drooling or unwanted oozing of the dental material from the syringe tip is prohibited subsequent to an extruding operation.

Another object is to provide an improved dental syringe in which all of the material contained within an elongated cartridge can be expressed therefrom.

Another object is to provide an improved dental syringe in which the syringe barrel is detachably connected and defines a readily disposable and expendible cartridge for containing the bulk supply of the dental material.

Another object is to provide a dental material packaging and dispensing system in which the proportion of the material necessary for a given procedure can be parcelled out directly from the bulk supply and still maintain sanitary conditions between the use on successive patients.

SUMMARY OF THE INVENTION

The foregoing objects and other features and advantages of this invention are attained by providing a dental syringe with a readily detachable tubular syringe barrel or cartridge which comprises the initial package in which a bulk supply of dental material is packaged, marketed and stored between uses, and which cartridge, when attached to a specifically constructed handle means and associated plunger defines an operative syringe assembly whereby the dental material can be readily dispensed directly from the bulk supply to the patient's tooth as needed and where needed, without any intervening procedures or operations. The cartridge comprises an elongated tubular barrel defining a reservoir for containing a supply of the bulk material. The rear end of the cartridge is open and it is sealed by a free floating piston which is displaceably mounted within the barrel to effect the extrusion of the dental material as it is displaced by a syringe plunger. The forward end of the cartridge is provided with a discharging orifice portion to which an expendable disposable nozzle tip is connected for use with different patients, and for imparting direction and precision to the positioning of the extrudant material. The rear end of the cartridge is provided with a fastening means e.g. screw threads by which it can be detachably connected to a handle portion of the syringe assembly.

In one form of the invention, the handle portion may comprise simply a finger grip or shield which may be fixed or detachably connected to the cartridge. A plunger is provided for insertion into the rear open end of the cartridge to effect the displacement of the piston to effect a corresponding extrusion of the material therefrom as may be needed.

In another form of the invention, the handle portion comprises a lever actuated handle to impart a mechanical advantage to the plunger so as to facilitate the extrusion of the viscous dental material with a minimum of effort. The lever actuated handle comprises a fixed handle member to which the cartridge is detachably connected intermediate the ends thereof. A second handle member is pivotally or hingedly connected to the first handle member so as to bear against the end of the plunger whereby the plunger is displaced as the handle members are squeezed toward one another. To fully express the material in the cartridge, the length of the plunger is rendered longitudinally extendible to allow large volumes of material to be extruded while utilizing a relative short throw of the movable handle member. Longitudinal adjustment of the plunger is effected by utilizing nesting telescoping plunger segments arranged to extend and distant accordingly.

The plunger is also provided with a valving means to relieve the back pressure imparted on the piston after an extrusion operation so as to prohibit any drooling or oozing of the dental material from the discharge end of the cartridge.

FEATURES

A feature of this invention resides in the dispensing of dental material in a cartridge which also functions as a component part of a simply constructed syringe assembly whereby the dental material can be readily and directly dispensed from its bulk supply as needed and where needed with a minimum of waste and/or effort.

Another feature resides in the provision of a cartridge for containing a bulk supply of dental material from which the material can be incrementally dispensed by syringing.

Another feature resides in an improved dental syringe assembly having a longitudinally extendable plunger for expressing relatively large volumes of dental material from a syringe assembly having a relatively short plunger or piston displacement.

Another feature resides in providing the plunger with a means for creating a vacuum on the rear end of the piston to relieve the pressure imparted to the dental material so as to prohibit drooling of the material upon termination of an extruding operation.

Another feature resides in the provision of a dental syringe assembly for directly dispensing a dental material from a bulk supply as needed through a disposable dispensing nozzle and thereby maintaining sanitary conditions between use on successive patients.

Other features and advantages will become more readily apparent when considered in view of the drawings and specifications in which FIG. 1 is a side sectional view of a syringe assembly illustrating the present invention.

DETAIL SPECIFICATION

Figure 1:
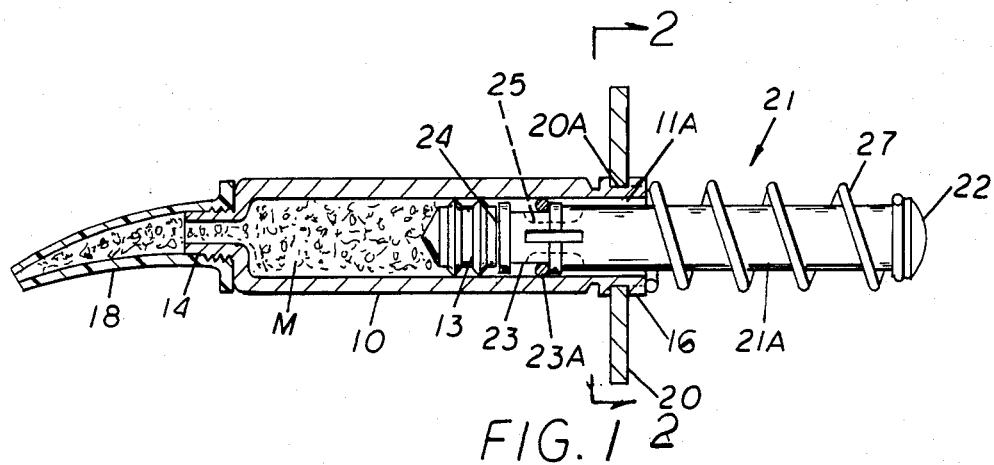
Figure 2:
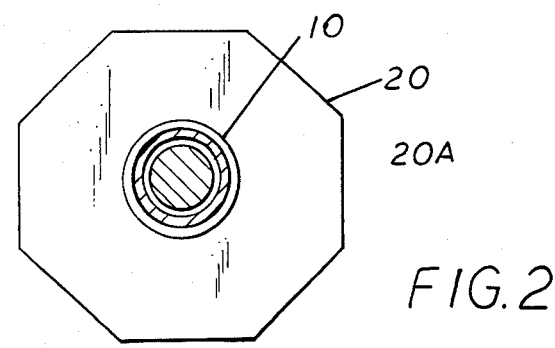
FIG. 2 is a section view taken along line 2—2 on FIG. 1.
Figure 4:
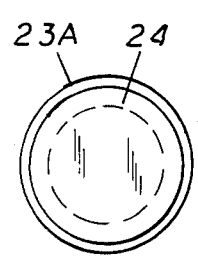
FIG. 4 is a left end view of the plunger means of FIG. 3.

Referring to the drawings, there is shown several dental syringe assemblies which comprise further advances over the syringe constructions disclosed in any prior patents and patent application herein above identified. The present invention relates to syringe construction in which relatively large volumes of dental materials, such as composite resins, impression materials, light activated materials and the like can be readily packaged in cartridges which are used as an integral part of a syringe assembly, whereby portions of the bulk material can be directly expressed as needed and where needed with a minimum of waste and/or effort and/or intervening measuring operations.

Figure 8:
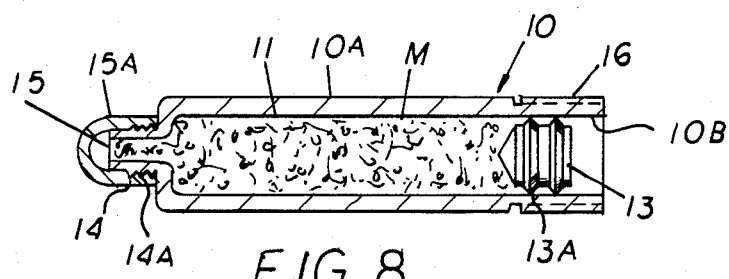
FIG. 8 is a detail view of the cartridge or syringe barrel as a package for a bulk supply of dental material.

As best seen in FIG. 8, the dental material M, e.g. light activated material may be packaged for distribution directly to the dentist in a light impervious cartridge 10 which comprises essentially an elongated barrel portion 10A having a full open rear end portion 10B. The elongated barrel portion 10A defines a reservoir or chamber 11 sized to receive a relatively large volume of dental material M. The rear end 10B is sealed by a freely floating or displaceably piston 13. The forward end of the tubular barrel portion 10A is provided with a projecting discharging end 14 terminating in a discharge orifice 15. The discharge orifice is initially sealed by an end cap 15A.

In the illustrated embodiment, the rear end 10B of the cartridge is formed with external threads 16 or the like, by which the cartridge 10 can be readily detachably connected to a handle means of a syringe assembly as will be herein described. An end cap 15A is detachably connected to the discharging end to seal the discharge orifice 15 when the cartridge is not in use as a syringe component. In the illustrated embodiment, the discharge portion 14 is provided with external threads or lands 14A by which the end cap 15A or nozzle tips 18 (as hereinafter described) can be positively secured thereto, either by frictional or by mechanical threading.

As seen in FIG. 8, the piston 13 is provided with one or more circumscribing seals 13A disposed in sealing relationship to the internal walls of chamber or reservoir 11.

Figure 3:
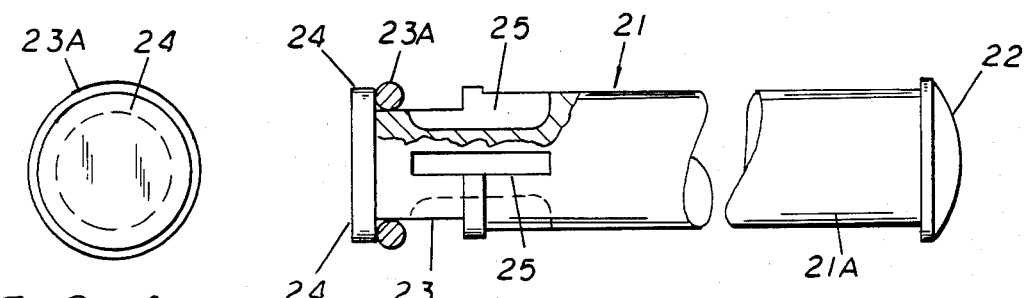
FIG. 3 is a detail side view of the plunger means.

Referring to FIGS. 1 and 3, the cartridge 10 containing the bulk supply of material M can be readily converted by the dentist to a dispensing syringe by attaching to the rear end of the cartridge 10 a finger grip or shield 20. In the illustrated embodiment, the shield 20 is provided with a threaded opening 20A, which can be readily threaded into the threads 16 of the cartridge. A plunger means 21 is disposed in the rear end of the cartridge 10 to bear against the piston 13 to complete the syringe assembly.

In the illustrated embodiment, the plunger means 21 comprises an elongated shank 21A sized to be received within the cartridge 10. One end of the plunger shank 21A is provided with an enlarged head 22 against which a dentist may push with his thumb to effect displacement of the piston 13 and resulting extrusion of the material M in advance of the piston 13. A spring 27 is coiled about the end of the shank 21 so as to be compressed between the plunger head 22 and the end of the cartridge 10 as shown. Thus, the spring 27 functions to normally bias the plunger 21 outwardly of the cartridge 10.

As best seen in FIG. 3, the forward end of the plunger shank 21A is provided with an annular groove 23 adjacent the blunt end 24 which presses against the piston 13. Floating in the reduced portion defining the groove 23 is a sealing O-ring 23A. As shown in FIG. 1, the O-ring 23A is disposed in sealing relationship with the internal bore of the cartridge immediately to the rear of the piston 13. The diameter of the shank 21 is slightly less than the internal diameter of the cartridge 10 so as to define an annular venting chamber 11A to the rear or right of the O-ring 23A as best seen in FIG. 1. Disposed about the shank 21, to the right of the O-ring 23A, as seen in FIGS. 1 and 3, are one or more vent slots 25. As described in my co-pending application, Ser. No. 314,768, filed Oct. 26, 1981, the O-ring 23A is displaceable within the groove 23 to valve the vent slots 25 depending on the direction of displacement of the shank 21.

In operation, on the extruding stroke of the plunger 21, i.e. when the plunger 21 is moved to the left as viewed in FIG. 1, the O-ring 23A is displaced to the right end of the groove 23, whereby the area to the rear of the piston 13 is vented through vent slots 25 to the rear of the cartridge. Upon the retraction or under the action of spring 27, the O-ring 23A is shifted to the left side of groove 23 to seal off the back side of the piston 13. Thus, as the plunger 21 is retracted or shifted to the right relative to the piston 13, as viewed in FIG. 1, a vacuum is created between the piston 13 and the end 24 of the plunger. The creation of the vacuum behind the piston thus relieves the back pressure on the piston 13 causing slight retraction thereof and thereby relieves the pressure which would otherwise cause the material M to drool slightly upon the termination of an extruding operation.

To precisely control the direction and placement of dispensing the material M, a readily disposable nozzle tip 18 may be detachably connected to the discharge end 14 of the cartridge 10. For dispensing light activated material, it will be understood that the cartridge 10 and the disposable nozzle tip 18 may be formed of light impervious or black material. The nozzle tips 18 may be constructed as described in my U.S. Pat. Nos. 3,581,399 and De. 226,767.

From the construction described, it will be apparent that the cartridge 10 in which the dental material is packaged, marketed or stored in bulk, can be readily converted for direct use into a syringe assembly by simply attaching thereto a finger grip or shield 20 and a plunger 21. By positioning the assembled syringe between the fore finger and index finger, and pressing on the head end 22 of the plunger with the thumb, the material 12 can be readily extruded through the discharge orifice and associated nozzle tip 18.

Figure 5:
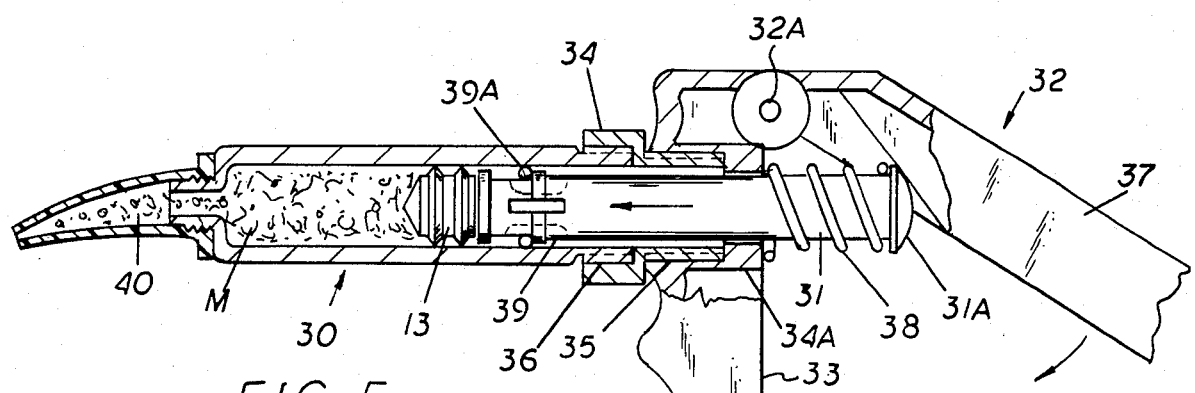
FIG. 5 is a side sectional view of a modified embodiment illustrating the parts in an extruding position.
Figure 6:
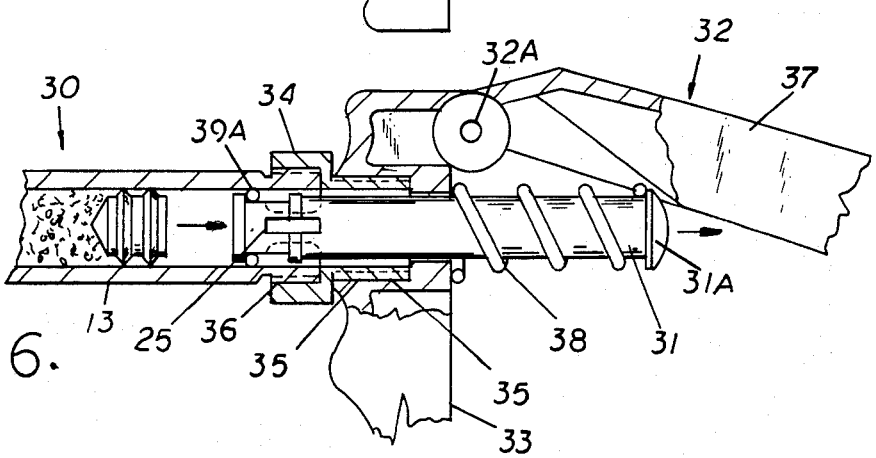
FIG. 6 is a view similar to FIG. 5, showing the portion at the end of an extrusion operation.
Figure 7:
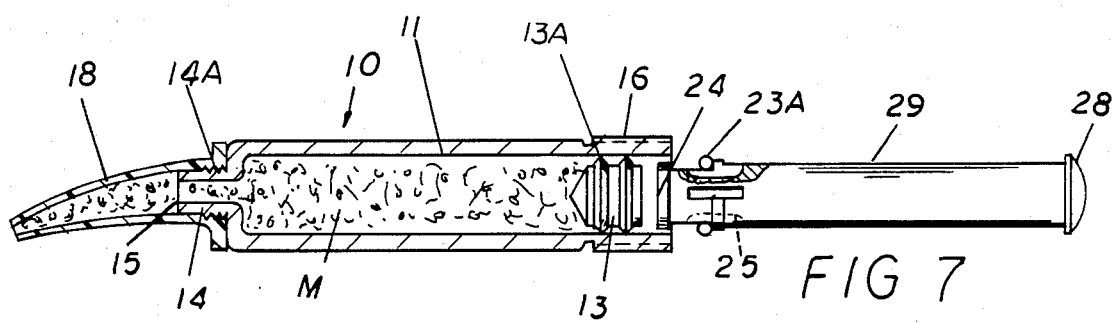
FIG. 7 is a detail, exploded view of the cartridge, plunger and disposable tip assembly.

FIGS. 5 and 6 illustrate a modified embodiment. In this embodiment, the cartridge assembly 30 is similar in construction and operation to the cartridge 10 herein described. In this form of the invention, the cartridge 30 is detachably connected to a modified handle construction to impart a mechanical advantage on the plunger 31, which is similar in construction as hereinbefore described with respect to FIGS. 1 and 3.

In this form of the invention, the handle means 32 comprises a first or fixed handle member 33. The handle member 33 provided with a barrel mounting means or adaptor 34 and/or plunger bore 34A disposed intermediate the length thereof. The end of the adaptor 34 is provided with threads 35 or other suitable means by which it is connected to bore 34A of the handle 32. The adapter or cartridge mount 34 is also provided with an internally threaded portion 36 to which the cartridge 30 can be readily detachably connected.

Pivotally connected about a pivot or junction 32A to the handle member 33 is a lever actuator or second handle member 37. The lever or handle member 37 in the operative position is disposed in bearing relation to the head end 31A of the plunger 31. A spring 38 coiled about the rear end of the plunger 31 exerts a spring bias on the plunger. In this form of the invention, the plunger 31 is displaced as the handle members 33 and 37 are squeezed toward one another. The plunger 31 may be constructed similar to that hereinbefore described, and as such will function in a manner as hereinbefore described. It will be understood that the plunger 31 may also be provided with venting means 39 and O-ring seal 39A similar to that hereinbefore described. A disposable tip 40 as hereinbefore described may also be used to precisely direct the extrudent material M where and as needed.

Figure 9:
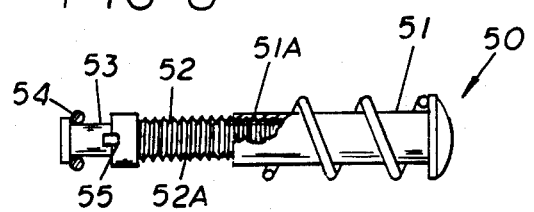
FIG. 9 is a side sectional view of a modified plunger assembly.

In the event that the throw of the handle means 32 is short relative to the length of the cartridge 30, the plunger assembly is modified as shown in FIG. 9. In this arrangement, the plunger means or assembly 50 comprises at least a pair of nested, telescoping members 51 and 52 which can be adjustably extended, as may be required to extrude virtually all of the material contained within the associated cartridge with a relatively short stroke of the handle means 32. As shown, the modified plunger 50 of FIG. 9 includes an external plunger section 51 and an internally nested inner section 52. The respective sections 51 and 52 are provided with complementary means for adjustably extending the sections 52, 51 between extended and distended positions. In the illustrated arrangement, the outer section 51 is provided with a series of internal threads 51A to mate with the external threads 52A of the inner section 52. It will be understood that other suitable complementary means may be provided for adjustably nesting and adjusting the respective members 51 and 52. The forward end of the plunger assembly 50 is also provided with a groove 53 and sealing ring 54 for valving vent slot 55 to provide for the anti-drooling feature as hereinbefore described with respect to FIGS. 1 and 5. With the plunger assembly 50 of FIG. 9, it will be apparent that, where the throw of the handle means is short, the material within the cartridge can nevertheless be totally expressed by incrementally lengthening the plunger assembly 50 as may be required. Thus, the plunger assembly 50 can be adjustably extended as the material of the cartridge is gradually diminished or used accordingly.

With the construction described, a dentist has total control over the amount of material required for a given procedure, and which material can be expressed or extruded from the bulky supply source, thereby eliminating any intermediate measuring requirements heretofore necessitated. It will be further understood that the various dental materials required for different procedures can be dispensed or marketed in cartridges which can be rendered readily interchangeable. Also, the respective colors used for composite resins and light activated materials can be color coded in their individual cartridge which further aids both the dentist and the manufacturer in storing and inventorying of the dental materials. Thus, the package in which the material is stored and marketed becomes a part of the tool by which it is dispensed. In the case of light activated materials, the present invention permits delivery of the desired material directly from the bulk supply to the tooth of the patient as needed without exposure to curing light by any intermediate measuring step. The described construction and method of packaging, storing and dispensing dental material thus eliminates waste and loss of time, while substantially enhancing the dental procedures and minimizing costs.

While the invention has been described with respect to several embodiments, it will be appreciated that variations and modifications may be made without departing from the spirit or scope of the invention. For example, it will be understood that where the illustrated embodiment discloses a threaded connection as in FIG. 1 of the handle means 20 to the cartridge 10 as at 16, it will be understood that other types of complementary fastening means may be employed such as a bayonnet connection, bonding, friction and the like. Also, other complementary nesting and/or extension means may be employed to extend and distend the plunger assembly of FIG. 9. Also, it will be understood that the adaptor 34 of FIGS. 5 and 6 can be made either as an integral part or a separate part of the handle means 33. Alternately, the handle part 33 may be formed with a base 34A which will directly accommodate and detachably receive the cartridge 30; by suitable complementary detachable fastening or coupling means.

What is claimed is:

1. A dental syringe for extruding dental materials comprising:
    a handle means and a cartridge adapted to contain a bulk supply of said dental material sufficient to perform a plurality of dental procedures whereby said cartridge defines the barrel portion of said syringe,
    said cartridge comprising an elongated barrel having a rear open end and a forward discharging orifice portion,
    a freely displaceable portion disposed in said barrel portion for sealing the rear end thereof,
    a plunger means adapted to extend into the rear open end of said barrel for engaging said piston,
    said plunger means having an end portion for engaging the rear of said piston for effecting the displacement of said piston within said barrel as said plunger means is activated to extrude a proportional amount of said material,
    a spring means for normally biasing said plunger means toward a retracted inoperative position and a valving means including a vent slot disposed on the end of said plunger means for engaging said piston for venting the area to the rear of the piston for creating a vacuum between said piston and said plunger to effect a pull back of said piston to relieve the back pressure of said material acting on said piston upon the termination of an extruding operation so as to prohibit any drooling of the material from the cartridge.

2. A dental syringe as defined in claim 1 wherein said valving means for relieving said back pressure comprises:
    a groove circumscribing at least a portion of said end portion of said plunger means,
    said venting slot, disposed in communication with said groove,
    a sealing ring disposed in said groove and in sealing relationship with said barrel and which is displaceable in said groove so as to valve said venting slot between an open position and a sealed position as said plunger means is displaced between an extruding position and a retracted position.

3. A dental syringe as defined in claim 2 and including a disposable nozzle tip removably connected to said discharged orifice portion for directing the extrudant material from said cartridge.

4. A dental syringe as defined in claim 3 wherein said handle means includes a finger grip connected intermediate the ends of said cartridge.

5. A dental syringe as defined in claim 3 wherein said handle means includes a first handle member having a bore intermediate the ends thereof,
    means for detachably connecting said cartridge to the bore of said first handle member,
    a second handle member pivotally connected to said first handle member for movement relative thereto when said first and second handle members are squeezed,
    and said plunger means having a head end portion disposed in bearing relationship with said second handle member whereby the displacement of said second handle member affects displacement of said plunger means and piston to extrude said dental material.

6. A dental syringe as defined in claim 1, wherein said plunger means includes at least a pair of nested telescoping members disposed so as to be adjusted between a nested retracted position and an extended protracted position whereby the length of said plunger means can be incrementally extended to provide for complete evacuation of the extruded material from the cartridge.

7. A dental syringe for extruding a viscous dental material comprising
    a handle means and a cartridge means,
    said cartridge means including an elongated barrel portion having an opened rear end and discharging orifice formed at the forward end thereof,
    said barrel portion being adapted to contain a bulk supply of said dental material,
    a freely mounted piston disposed in sliding relationship within said barrel portion, said piston forming a seal at said rear end of said barrel portion whereby the displacement of said piston effects the extrusion of the material from said barrel corresponding to the displacement of said piston,
    a plunger slidably mounted in said barrel portion disposed in engaging position with said piston to effect the displacement of said piston longitudinally of said barrel portion as said plunger is actuated,
    means for normally biasing said plunger toward an inoperative position,
    and a valving means including a vent slot disposed on the end of said plunger for engaging said piston for venting the area to the rear of the piston for creating a vacuum between said piston and said plunger to effect a pull back of said piston to relieve the back pressure of said material acting on said piston upon the termination of an extruding operation so as to prohibit any drooling of the material from said cartridge means.

8. A dental syringe as defined in claim 7 and including a disposable nozzle detachably connected to the discharge orifice of said cartridge means.

9. A dental syringe as defined in claim 7 where said handle means and said barrel portion of said cartridge means have complementary fastening means for detachably connecting said cartridge means to said handle means.

10. A dental syringe as defined in claim 7 wherein said handle means includes a radially extending finger shield fixedly connected to said cartridge means intermediate the length thereof.

11. A dental syringe as defined in claim 7 wherein said handle means includes a first handle member having a barrel mounting means disposed intermediate the ends thereof, said barrel portion being detachably connected to said mounting means, and a second handle member and means for pivotally connecting said second handle member to said first handle member whereby the displacement of said handle member effects a displacement of said plunger.

12. A dental syringe for extruding a viscous dental material comprising:

a handle means and a cartridge means, said cartridge including an elongated barrel portion having an open rear end and discharging orifice formed at the forward end thereof, said barrel portion being adapted to contain a supply of said dental material, a freely mounted piston disposed in sliding relationship within said barrel portion, said piston forming a seal in said rear end of said barrel portion whereby the displacement of said piston effects the extrusion of the material from said barrel corresponding to the displacement of said piston, a plunger slidably mounted in said barrel portion disposed in engaging position with said piston to effect the displacement of said piston longitudinally of said barrel portion, means for normally biasing said plunger towards an inoperative position, and means disposed on the end of said plunger for creating a vacuum between said piston and said plunger to relieve the back pressure on said piston upon the termination of an extruding operation so as to prohibit any drooling of the material from said cartridge, said plunger comprising at least a pair of nested telescopic members moveable between a relative extended position and a retracted position, and means for incrementally adjusting said telescopic members between said extended and retracted positions, wherein one of said telescopic members has a tip end having a reduced annular portion, a vent means, and a displaceable sealing means disposed on said annular portion for valving said vent means between an open and closed position as said plunger is displaced relative to said barrel portion.

13. A dental syringe for the extrusion and placement of a dental material in a dental restorative procedure comprising a handle means and a disposable cartridge adapted to contain a bulk supply of a dental extrudant material, said handle means including a first relatively fixed member, said first member having a mounting bore extending generally normal to the longitudinal axis thereof, said mounting bore being disposed intermediate the length of said first handle member, a second handle member pivotally connected to said second handle member whereby said second handle member is pivoted toward said first handle member during an extruding operation, and said disposable cartridge having an elongated barrel portion defining a reservoir for containing a bulk supply of the extrudant dental material, said barrel portion having an open rear end portion and a forward discharging orifice portion, external fastening means circumscribing the rear end of said cartridge for detachably securing said cartridge to the mounting bore of said fixed handle member, a displaceable piston disposed in said barrel portion for sealing the rear open end of said barrel, a plunger means slidably disposed in said mounting bore for enegagement with said piston, said plunger means having a head end portion adapted to be disposed in bearing relationship with said second handle member, said plunger means having a valving means including a vent slot on the forward end portion arranged to effect the displacement of said piston when said handle members are squeezed together, for imparting a negative pressure between the rear of said piston and said forward end of said plunger for effecting a pull back of said piston upon the release of said extruding pressure for relieving the back pressure of the material imparted on said piston during an extruding operation so as to prohibit any drooling of the extrudant dental material, and a spring means operating on said plunger for normally biasing said plunger toward an inoperative position.

14. A dental syringe as defined in claim 1 and including a disposable nozzle tip detachably connected to said discharge orifice for directing the extrudant material therefrom.

* * * * *

UNITED STATES PATENT AND TRADEMARK OFFICE
CERTIFICATE OF CORRECTION

PATENT NO. : 4,492,576
DATED : January 8, 1985
INVENTOR(S) : William B. Dragan

It is certified that error appears in the above-identified patent and that said Letters Patent is hereby corrected as shown below:

In Claim 1, Column 7, line 28, "displaceable portion" should read --displaceable piston--.

Signed and Sealed this

First Day of October 1985

[SEAL]

Attest:

Attesting Officer

DONALD J. QUIGG

Commissioner of Patents and
Trademarks—Designate